(12) United States Patent
Ueda

(10) Patent No.: US 7,906,075 B2
(45) Date of Patent: Mar. 15, 2011

(54) PIPETTE TIP RACK AND PIPETTE TIP ASSEMBLY

(75) Inventor: Makoto Ueda, Kakogawa (JP)

(73) Assignee: Sysmex Corporation, Kobe (JP)

( * ) Notice: Subject to any disclaimer, the term of this patent is extended or adjusted under 35 U.S.C. 154(b) by 753 days.

(21) Appl. No.: 11/258,993

(22) Filed: Oct. 27, 2005

(65) Prior Publication Data

US 2006/0093530 A1    May 4, 2006

(30) Foreign Application Priority Data

Nov. 2, 2004  (JP) ................... 2004-318665

(51) Int. Cl.
*B01L 3/00* (2006.01)
*B65D 1/34* (2006.01)
*B65D 1/36* (2006.01)

(52) U.S. Cl. .......... 422/102; 422/99; 422/100; 206/562; 206/563; 206/564

(58) Field of Classification Search .......... 422/99–100, 422/102; 206/557, 561, 562–565
See application file for complete search history.

(56) References Cited

U.S. PATENT DOCUMENTS

| | | | | |
|---|---|---|---|---|
| 5,232,669 A * | 8/1993 | Pardinas | .................... | 422/100 |
| 5,318,753 A * | 6/1994 | Honda | .................... | 422/104 |
| 5,392,914 A * | 2/1995 | Lemieux et al. | .................... | 206/499 |
| 5,441,702 A * | 8/1995 | Lemieux et al. | .................... | 422/100 |
| 5,456,360 A * | 10/1995 | Griffin | .................... | 206/443 |
| 5,487,997 A * | 1/1996 | Stolp | .................... | 436/54 |
| 5,612,000 A * | 3/1997 | Lemieux | .................... | 422/100 |
| 5,622,676 A * | 4/1997 | Lind | .................... | 422/104 |
| 5,630,988 A * | 5/1997 | Stolp | .................... | 422/100 |
| 5,827,745 A * | 10/1998 | Astle | .................... | 436/54 |
| 5,882,603 A * | 3/1999 | Taggart | .................... | 422/104 |
| 5,948,362 A * | 9/1999 | Steinbrenner et al. | .................... | 422/100 |
| 6,007,779 A * | 12/1999 | Lemieux et al. | .................... | 422/100 |
| 6,019,225 A * | 2/2000 | Kalmakis et al. | .................... | 206/563 |
| 6,164,449 A * | 12/2000 | Lahti | .................... | 206/499 |
| 6,221,317 B1 * | 4/2001 | Carl | .................... | 422/104 |
| 6,286,678 B1 * | 9/2001 | Petrek | .................... | 206/443 |
| 6,328,933 B1 * | 12/2001 | Labriola et al. | .................... | 422/104 |
| 6,405,870 B1 * | 6/2002 | Lahti et al. | .................... | 206/499 |

(Continued)

FOREIGN PATENT DOCUMENTS

DE    198 52 165 A1    11/1998

(Continued)

*Primary Examiner* — Brian R Gordon
(74) *Attorney, Agent, or Firm* — Birch, Stewart, Kolasch & Birch, LLP

(57) ABSTRACT

The pipette tip rack for detachably housing a plurality of pipette tips used in a liquid dispensing apparatus for dispensing liquid comprises a rack body comprising a pipette tip supporting portion for detachably supporting the pipette tips, and a pipette tip housing portion disposed below the pipette tip supporting portion having a plurality of pipette tip inserting holes, and a lid member detachably attached to the rack body for covering a root portion of the pipette tip inserted into the hole. The rack body includes a grasping portion grasped by a user when the pipette tip rack is set to the liquid dispensing apparatus in a state in which the lid member is attached to the rack body.

9 Claims, 16 Drawing Sheets

U.S. PATENT DOCUMENTS

| | | |
|---|---|---|
| 6,410,278 B1 | 6/2002 | Notomi et al. |
| 6,514,466 B2 * | 2/2003 | Labriola et al. ............... 422/104 |
| 6,534,015 B1 | 3/2003 | Viot et al. |
| 6,852,283 B2 * | 2/2005 | Acosta et al. .................... 422/65 |
| 7,060,226 B1 * | 6/2006 | Jessop et al. .................. 422/100 |
| 7,169,361 B2 * | 1/2007 | Arnold et al. .................. 422/100 |
| 7,220,590 B2 * | 5/2007 | Moritz et al. ................... 436/49 |
| 2001/0012492 A1 * | 8/2001 | Acosta et al. .................... 422/65 |
| 2003/0129089 A1 * | 7/2003 | Arnold et al. .................... 422/63 |
| 2005/0082243 A1 * | 4/2005 | Lahti et al. ...................... 211/74 |

FOREIGN PATENT DOCUMENTS

| | | |
|---|---|---|
| EP | 0 339 557 A2 | 11/1989 |
| JP | 9-127128 A | 5/1997 |
| JP | 11-2590 A | 1/1999 |
| JP | 2001-157847 A | 6/2001 |
| WO | WO-92/01514 A1 | 2/1992 |
| WO | WO-00/24513 A1 | 5/2000 |
| WO | WO-02/20375 A2 | 3/2002 |
| WO | WO-03/064271 A2 | 8/2003 |

* cited by examiner

PIPETTE TIP RACK AND PIPETTE TIP ASSEMBLY

FIELD OF THE INVENTION

The present invention relates to a pipette tip rack and a pipette tip assembly, especially to the pipette tip rack and the pipette tip assembly for detachably housing a dispensing pipette tip used in a liquid dispensing apparatus for dispensing liquid.

BACKGROUND OF THE INVENTION

Conventionally, a pipette tip rack capable of setting a plurality of dispensing pipette tip to a liquid dispensing apparatus or the like at a same time is known.

A pipette tip rack for inserting dispensing pipette tips to a plurality of holding holes provided on an automatic trace analysis apparatus having a dispense function at a same time, is disclosed in Japanese Laid-Open Patent Application Publication No. 2001-157847. An upper surface plate for covering head side of the pipette tip is detachably attached to the conventional pipette tip rack disclosed this patent publication.

And a rack capable of being set to a dispensing apparatus with multiple pipette tips contained therein is disclosed in Japanese Laid-Open Patent Application Publication No. H11-2590. The disclosed conventional rack is formed in a box-shape capable of containing a pipette tip end portion of the pipette tip.

However, in the conventional pipette tip rack disclosed in Japanese Laid-Open Patent Application Publication No. 2001-157847, since the pipette tip rack is set to the automatic trace analysis apparatus, in a manner in which a cover covering an end side of the pipette tip is not attached, the end side of the pipette tip is problematically contaminated when a user sets the pipette tip rack to the automatic trace analysis apparatus. And, in the pipette tip rack disclosed in the patent document NO. 1, since the pipette tip rack is not provided with a grasping portion, there is a problem that the pipette tip rack is hard to be grasped when a user set the pipette tip rack to the automatic trace analysis device.

And, in the conventional rack disclosed in Japanese Laid-Open Patent Application Publication No. H11-2590, since the rack is not provided with a lid for covering a head side of the multiple pipette tips, the head side of the pipette tip is problematically contaminated when a user sets the rack to the dispensing apparatus. And, in the rack disclosed in the patent document NO. 2, since the rack is not provided with a grasping portion, there is a problem that the rack is difficult to be grasped when a user sets the rack to the dispensing apparatus.

And, as described above, when the dispensing pipette tip used in an analysis apparatus such as the liquid dispensing apparatus, this may negatively affect a result of analysis, so that it is difficult to perform a correct analysis. Particularly in the analysis apparatus for inspecting nucleic acid by amplifying the same, when a degrading enzyme such as saliva of human beings attaches the dispensing pipette tip, this largely affect amplification of the nucleic acid, so that it is difficult to perform a correct analysis.

SUMMARY OF THE INVENTION

The scope of the present invention is defined solely by the appended claims, and is not affected to any degree by the statements within this summary.

The present invention has been achieved in order to solve the above-described problems. It is an object of the present invention to provide a pipette tip rack capable of preventing a dispensing pipette tip from contaminating when the pipette tip is set to a liquid dispensing apparatus, and of being set to the liquid dispensing apparatus by being easily grasped.

DETAILED DESCRIPTION OF THE PREFERRED EMBODIMENTS

The preferred embodiments of the present invention are described hereinafter with reference to the drawings.

Figure 1:
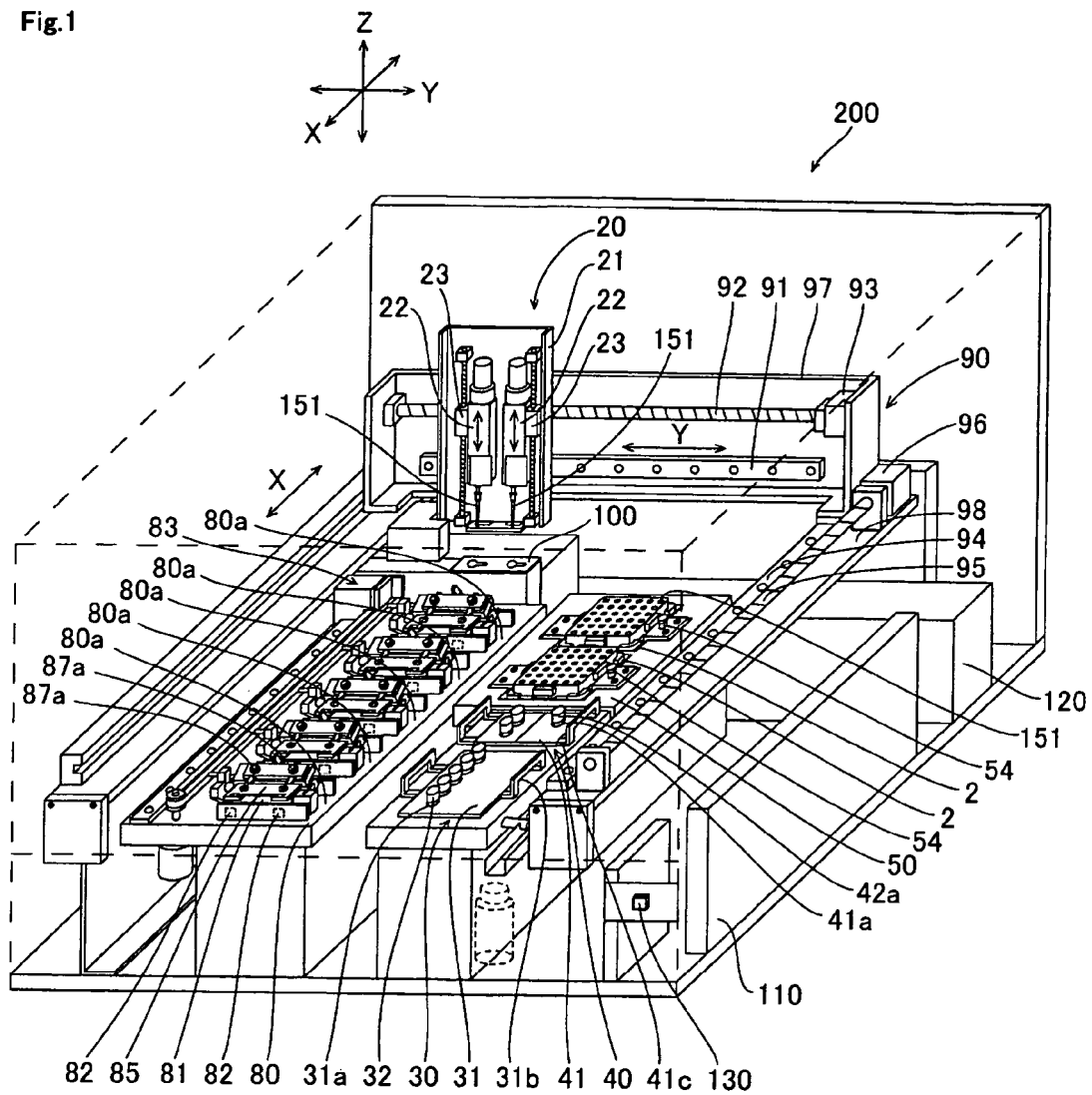
FIG. 1 is a perspective view showing an entire structure of a liquid dispensing apparatus (gene amplification detection apparatus) to which a pipette tip rack according to an embodiment of the present invention is mounted.
Figure 2:
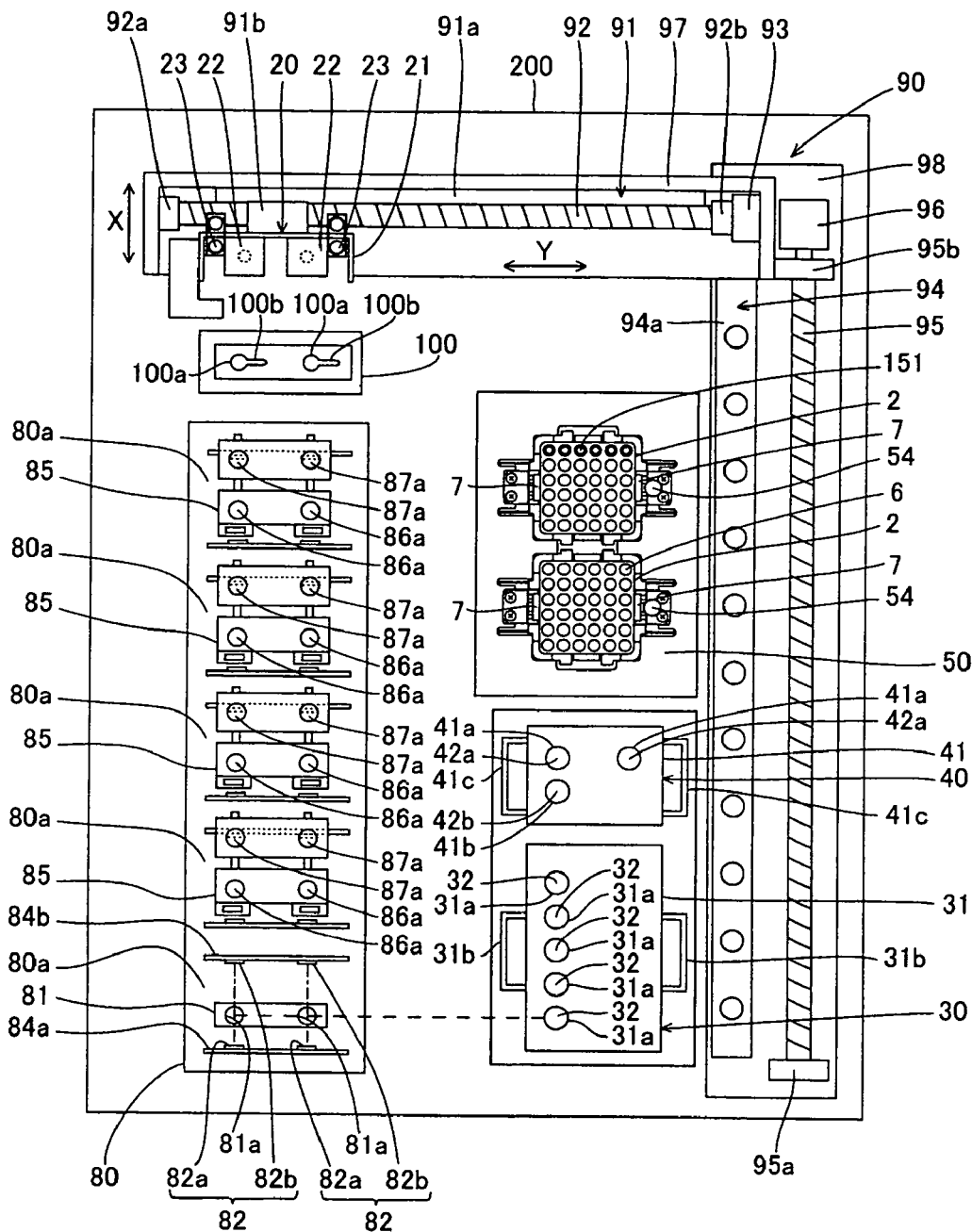
FIG. 2 is a plan view showing the entire structure of the liquid dispensing apparatus to which the pipette tip rack according to an embodiment of the present invention is mounted shown in FIG. 1.
Figure 10:
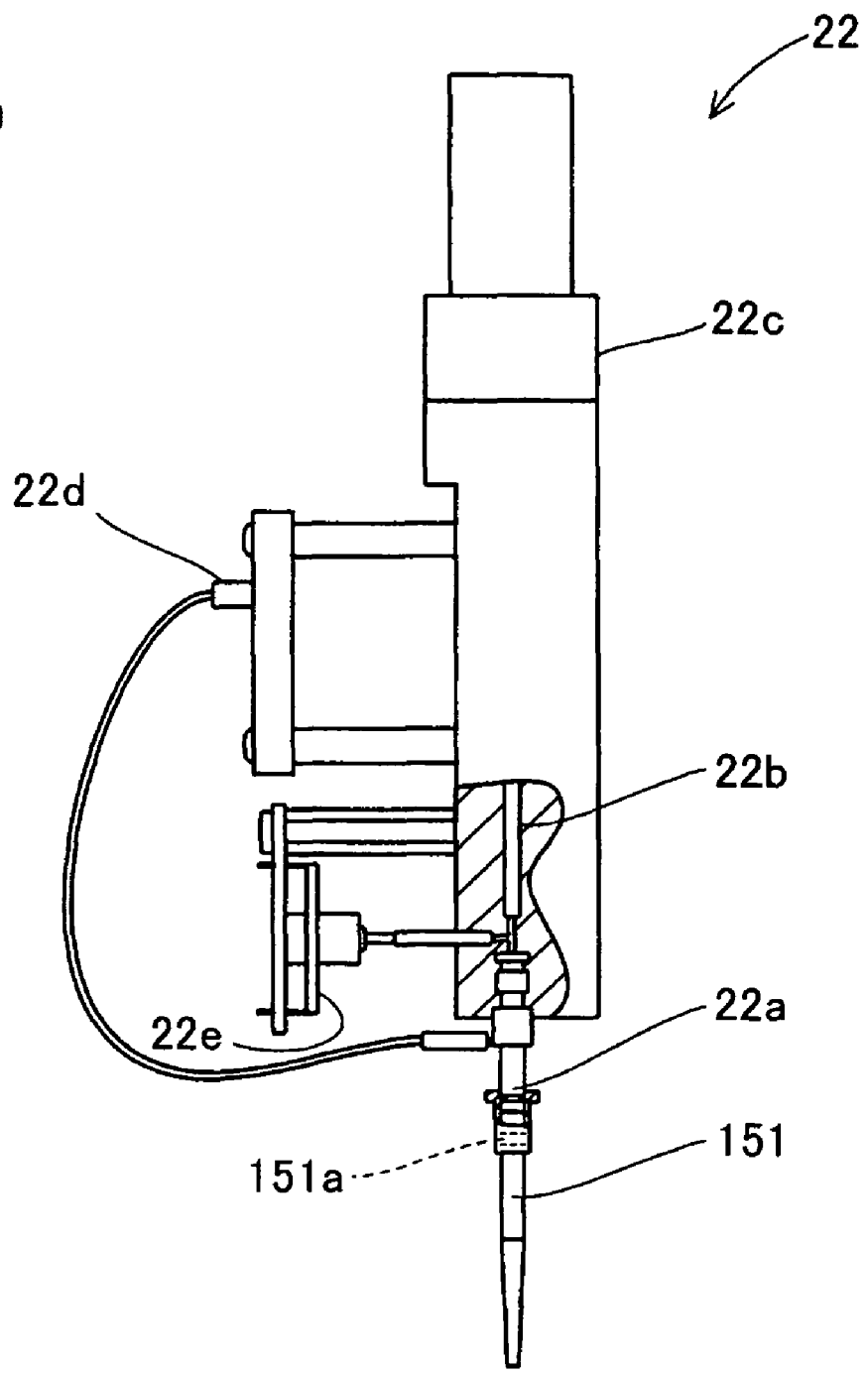
FIG. 10 is a schematic view showing a structure of a syringe portion of the liquid dispensing apparatus shown in FIG. 1.

FIGS. 1 and 2 are a perspective view and a plan view, respectively, showing an entire structure of a liquid dispensing apparatus (gene amplification detecting apparatus) to which a pipette tip rack according to an embodiment of the present invention is attached. FIGS. 3 to 9 are perspective views showing a pipette tip rack according to an embodiment of the present invention. FIG. 10 is a schematic view showing a structure of a syringe portion of the liquid dispensing apparatus shown in FIG. 1. FIGS. 11 to 14 are perspective views showing a structure of a pipette tip set portion of the liquid dispensing apparatus shown in FIG. 1. In this embodiment, a gene amplification detection apparatus is described as an example of the liquid dispensing apparatus in which the pipette tip rack according to an embodiment of the present invention is used. The gene amplification detection apparatus according to this embodiment is a apparatus for supporting a diagnosis of cancer metastasis in tissue resected in a cancer operation, and this detects tumor-derived nucleic acid (mRNA) existing in resected tissue, by amplifying the same by using a LAMP (Loop-mediated Isothermal Amplification) method (Eiken Chemical Co., Ltd.) and measuring a turbidity of a solution generated in an amplification. Detail of the LAMP method is disclosed in U.S. Pat. No. 6,410,278.

Figure 8:
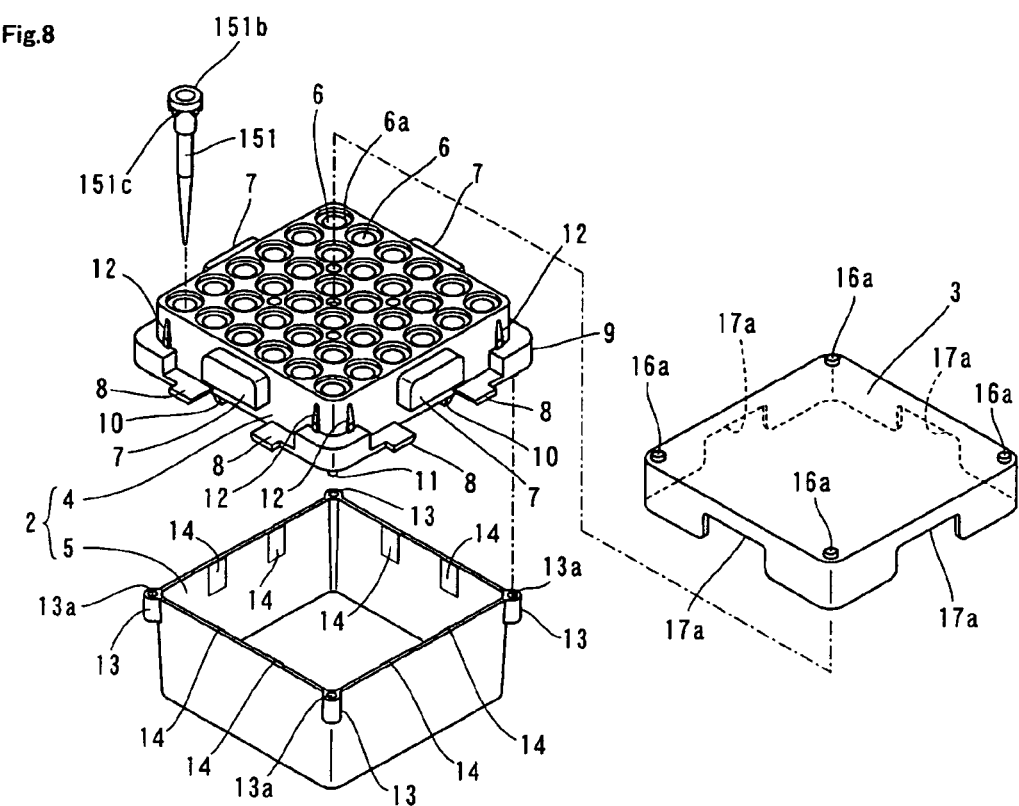
FIG. 8 is a perspective view showing a condition in which the pipette tip rack according to an embodiment shown in FIG. 3 is disassembled.
Figure 9:
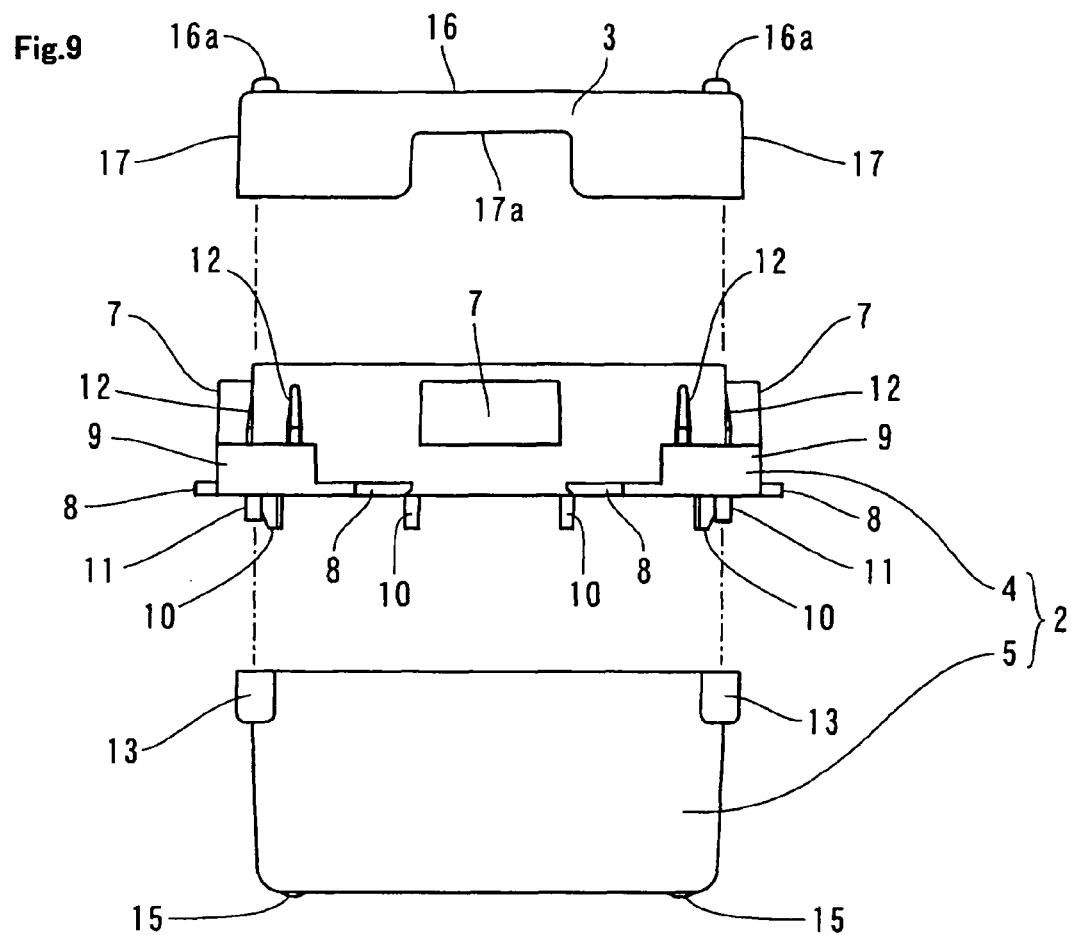
FIG. 9 is a front view showing a condition in which the pipette tip rack according to an embodiment shown in FIG. 5 is disassembled.

First, an entire structure of a liquid dispensing apparatus (gene amplification detection apparatus) 200 in which a pipette tip rack 1 according to an embodiment of the present invention is used, is described in reference to FIGS. 1, 8, and 10. The liquid dispensing apparatus (gene amplification detection apparatus) 200 comprises a dispensing mechanism portion 20, a sample container setting portion 30, a reagent container setting portion 40, a pipette tip set portion 50, a reaction detection portion 80 composed of five reaction detection blocks 80a, a transfer portion 90 for transferring the dispensing mechanism portion 20 in the X-axis and Y-axis directions, and a pipette tip rejecting portion 100, as shown in FIG. 1. The pipette tip rack 1 according to an embodiment of the present invention is set to the above-described pipette tip set portion 50. The liquid dispensing apparatus (gene amplification detection apparatus) 200 is configured to control the apparatus by means of a micro computer (CPU), and contains a control portion 111 for controlling an input from and an output to outside the apparatus, and a power supply portion 120 for supplying electric power to an entire apparatus including the control portion 110, as shown in FIG. 1. And, the liquid dispensing apparatus (gene amplification detection apparatus) 200 is provided with an emergency stop switch 130 on a predetermined position of a front face thereof. A pipette tip 151 used in the liquid dispensing apparatus 200 is formed by a conductive resin material containing carbon, and a filter 151a is attached to inside thereof, as shown in FIG. 1. The filter 151a is configured to prevent liquid from accidentally flow into a pump portion 22b. And, the pipette tip 151 has a flange portion 151b as shown in FIG. 8. A rib 151c for reinforcement is formed integrally with the flange portion 151b.

Figure 3:
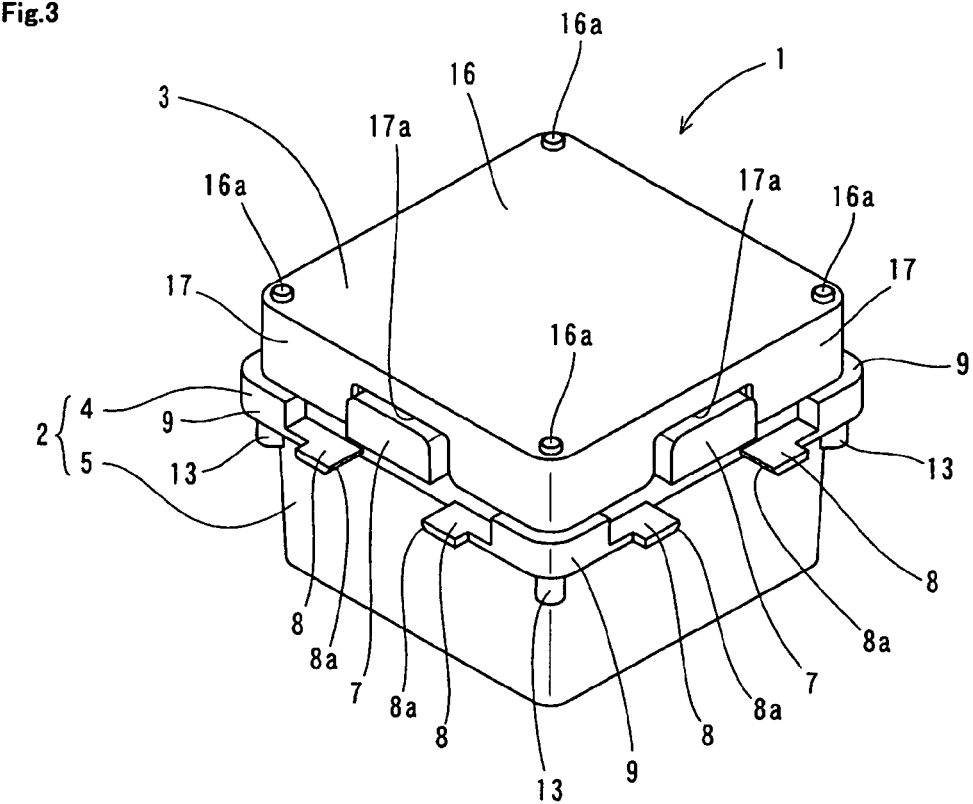
FIG. 3 is a perspective view showing a pipette tip rack according to an embodiment of the present invention.
Figure 4:
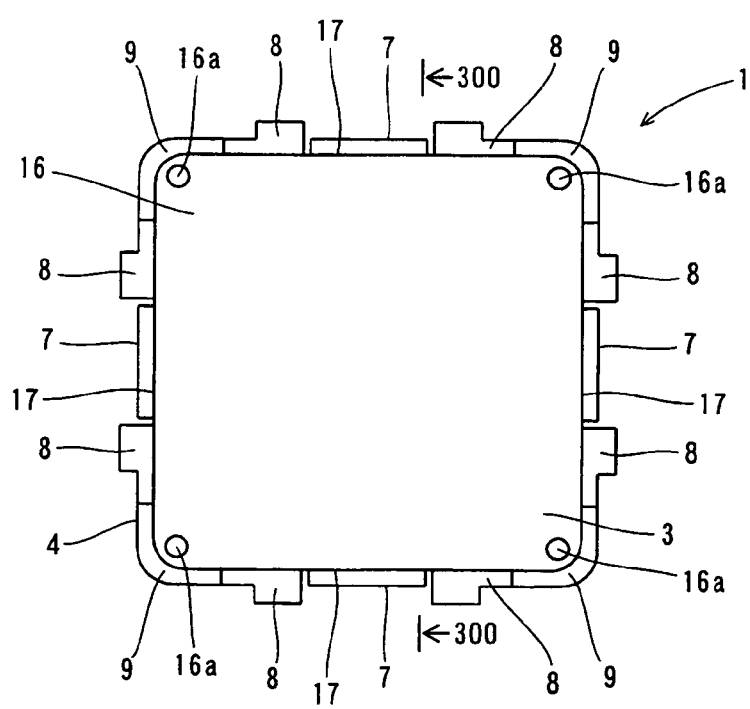
FIG. 4 is a top view showing the pipette tip rack according to an embodiment shown in FIG. 3.

Herein, a structure of the pipette tip rack 1 according to an embodiment of the present invention is described in detail in reference to FIGS. 3 to 9, and 13. A resin pipette tip rack 1 according to an embodiment of the present invention comprises a rack body 2 and a lid member covering an upper portion of the rack body 2, as shown in FIG. 3. And the rack body 2 comprises a pipette tip supporting member 4 for supporting the pipette tip 151 (see FIG. 8), and a pipette tip housing member 5 attached to a lower portion of the pipette tip supporting member 4. The rack body 2 and the lid member 3 according to this embodiment are square as seen from above, as shown in FIG. 4. And, the lid member 3 and the pipette tip housing member 5 are formed by a semitransparent resin material (polypropylene), so that inside thereof are visible from outside.

Figure 5:
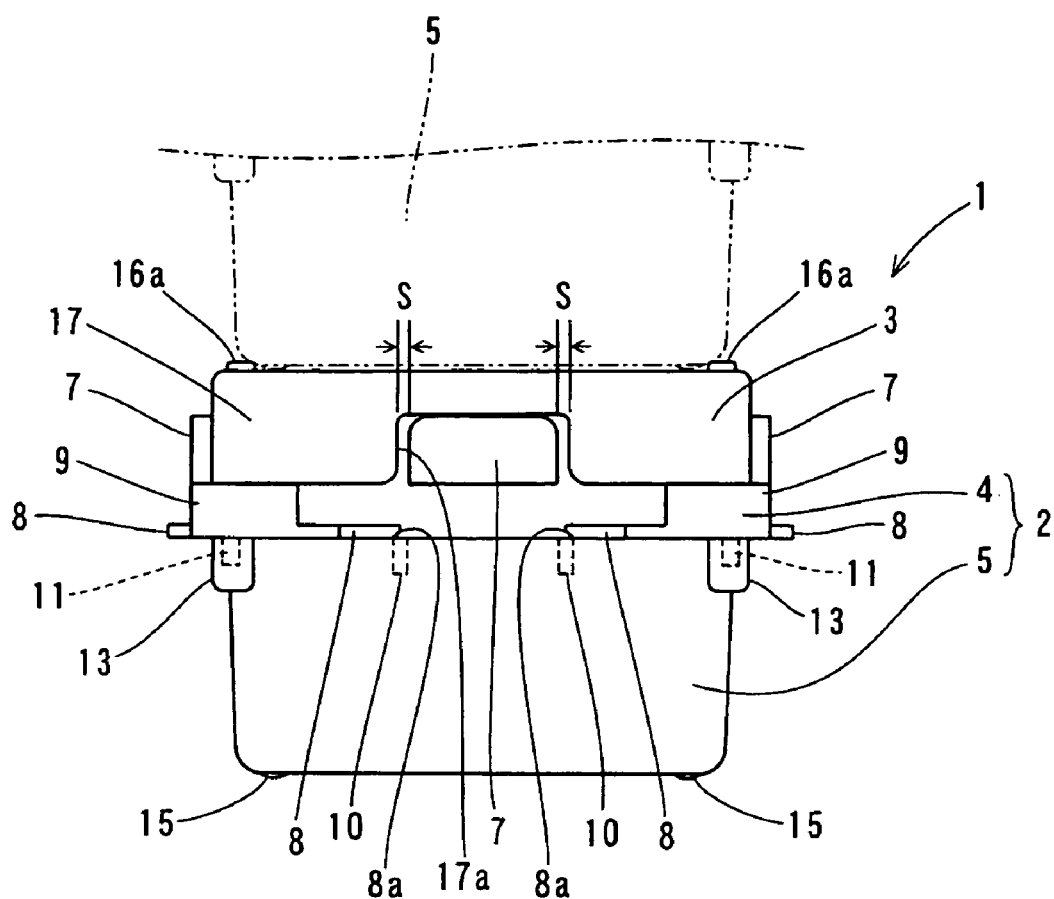
FIG. 5 is a front view showing the pipette tip rack according to an embodiment shown in FIG. 3.
Figure 6:
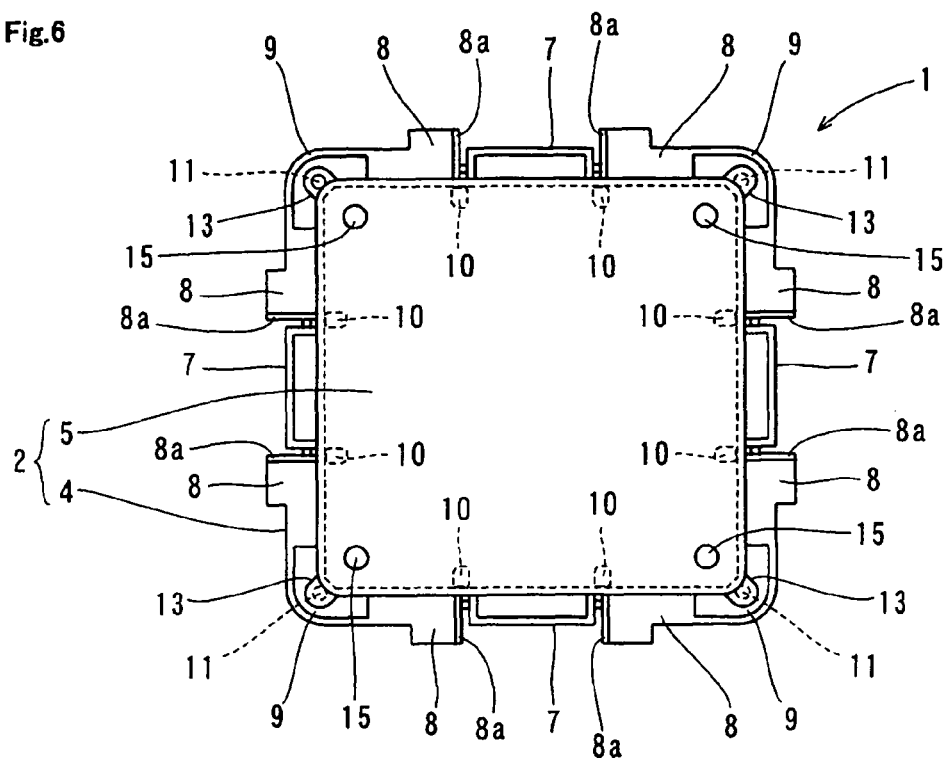
FIG. 6 is a bottom view showing the pipette tip rack according to an embodiment shown in FIG. 3.
Figure 7:
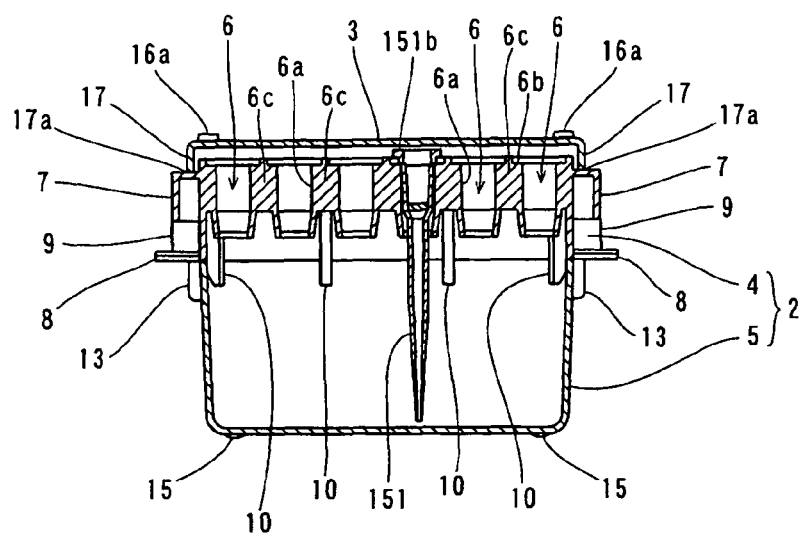
FIG. 7 is a cross-sectional view taken along a line 300-300 in FIG. 4.

And in this embodiment, the pipette tip housing member 4 includes a plurality of pipette tip inserting portions 6 (see FIG. 8), four grasping portions 7, four pairs of engaging portions (see FIG. 4), four reinforcement ribs 9 (see FIG. 4), four pairs of deflection preventing portions 10 (see FIG. 6), four engaging protruding portions 11 (see FIG. 6), and eight positioning ribs 12, as shown in FIGS. 4, 6, 8 and 9. Each of the pipette tip inserting portions 6 has a pipette tip inserting hole 6a into which the pipette tip 151 is to be inserted as shown in FIG. 7, and is cylindrically formed so as to extend downward from an upper surface of the pipette tip housing member 4. The pipette tip inserting hole 6a is provided with a step portion 6b in the vicinity of an opening thereof. The step portion 6b of the pipette tip inserting hole 6a is formed such that the flange portion 151b of the pipette tip 151 to be described later fits into the same. And, a reinforcement rib 6c is formed between adjacent cylindrical pipette tip inserting portions 6. Thirty-six pipette tip inserting portions 6 are formed on the pipette tip supporting member 4 according to this embodiment shown in FIG. 8, in a matrix arrangement with six lines in a longitudinal direction and six lines in a lateral direction. Each of the grasping portions 7 is formed on four side surfaces of the pipette tip supporting member 4 in the vicinity of a center portion of the surfaces, as shown in FIGS. 4 and 6. Each of the four grasping portions 7 is disposed on corresponding position in four directions with respect to a planar center of the pipette tip supporting member 4 (rack body 2). The grasping portion 7 is formed so as to protrude outwardly over a side surface portion of the lid member 3 when the lid member 3 is attached to the rack body. Each of the engaging portions 8 is formed so as to protrude laterally from a lower end position of the side surface of the pipette tip supporting member 4. Each pair of the engaging members 8 is provided on each of the four side surfaces of the pipette tip supporting member 4, for fixing the rack body 2 to the pipette tip set portion 50 of the liquid dispensing apparatus 200. The engaging portion 8 is provided with a slant portion 8a on a position abutting against a rack engaging portion 60 of the pipette tip set portion 50 to be described later (see FIG. 13), as shown in FIG. 5. And, each of four pairs of engaging portions 8 is disposed on corresponding position in four directions with respect to the planar center of the pipette tip supporting member 4 (rack body 2).

And the reinforcement rib 9 is formed so as to protrude outwardly over a lower end position of a corner portion formed by two adjacent side surfaces of the pipette tip supporting member 4. The reinforcement rib 9 is formed so as to connect two engaging portions 8 each formed on adjacent side surfaces, for reinforcing the engaging portions 8. Each of deflection preventing portions 10 is formed so as to protrude downward from a lower end position of the side surface of the pipette tip supporting member 4. Each pair of the deflection preventing portion 10 is provided on each of the four side surfaces of the pipette tip supporting member 4 with a predetermined space therebetween as shown in FIG. 6, for preventing a side surface of the pipette tip housing member 5 attached to the pipette tip supporting member 4 from inwardly deflecting. Each of the engaging protruding portions 11 is formed so as to protrude downward from a lower end position of the corner portion of the pipette tip supporting member 4, as shown in FIG. 8. The engaging protruding portion 11 of the pipette tip supporting member 4 and a hole 13a of the engaging portion 13 of the pipette tip housing member 5 to be described later engage with each other, thereby detachably attaching the pipette tip housing member 5 to the pipette tip supporting member 4. Each of the positioning ribs 12 is formed on the side surface of the pipette tip supporting member 4 so as to connect with an upper portion of the reinforcement rib 9 of the pipette tip supporting member 4. The positioning rib 12 is formed such that a protruding amount thereof from the side surface of the pipette tip supporting member 4 decreases in a direction from a lower portion to an upper portion thereof, and is configured to position the lid member 3 when the lid member 3 is attached to the rack body 2.

The pipette tip housing member 5 is formed in a box shape including a square bottom surface and four side surfaces extending upward from an outer periphery of the bottom surface. The pipette tip housing member 5 has such a housing depth that a pipette tip end portion of the pipette tip 151 supported by the pipette tip supporting member 4 does not contact with an inner side of the bottom surface of the pipette tip housing member 5. And, the pipette tip housing member 5 includes four engaging portions 13, four pairs of reinforcement portions 14 (see FIG. 8), and four supporting portions 15, as shown in FIGS. 6 and 8. Each of the engaging portions 13 is formed on one of four corner portions formed by four side surfaces of the pipette tip housing member 5. Each of the engaging portions 13 has a hole 13a into which the engaging protruding portion 11 of the pipette tip supporting member 4 is inserted. Each pair of the reinforcement portions 14 is formed on an upper end position of an inner side of four side surfaces of the pipette tip housing member 5. The reinforcement portion 14 is formed on a position against which the deflection preventing portion 10 of the pipette tip supporting member 4 abuts when the pipette tip housing member 5 is attached to the pipette tip supporting member 4. Each of the supporting portions 15 is formed in the vicinity of four corner portions formed on an outer side of the bottom surface of the pipette tip housing member 5 so as to protrude downward. Since the four supporting members 15 allow the bottom surface of the pipette tip housing member 5 to be supported not by a surface but at four points, the pipette tip rack 1 can be supported more stably than in a case in which the pipette tip rack 1 is supported by a surface, when the pipette tip rack 1 is placed on an uneven surface.

And the lid member 3 comprises a square upper surface portion 16 and four side surface portions 17 extending downward from an outer periphery of the upper surface portion 16, as shown in FIGS. 4 and 8. The upper surface portion 16 of the lid member 3 includes four position restrict bosses 16a formed on four corner portions of the upper surface portion 16. The four position restrict bosses 16a are provided for controlling a placing position of an upper pipette tip rack 1 with regard to a lower pipette tip rack 1 when a plurality of pipette tip racks 1 are stacked, as shown in FIG. 5. The side surface portion 17 of the lid member 3 includes four notches 17a each formed on four side surface portions 17 as shown in FIG. 8. Four notches 17a are provided for housing four grasping portions 7 of the pipette tip supporting member 4 within the notches 17a, when the lid member 3 is attached to the rack body 2. The notch 17a is formed so as to engage with the grasping portion 7 of the rack body 2 with a predetermined allowance (space S) at right and left thereof. The lid member 3 is formed so as to be attached to the rack body 2 with a predetermined allowance between the same and the four side surface portions 17 of the lid member 3, and between the same and the eight positioning ribs 12 of the pipette tip supporting member 4 of the rack body 2. Thereby, the lid member 3 is easily attached to and detached from the rack body 2.

And the dispensing mechanism portion 20 shown in FIG. 1 comprises an arm portion 21 movable in the X-axis and the Y-axis directions (horizontal direction) by means of a transfer portion 90, two syringe portions 22 independently movable in the Z-axis direction (vertical direction) with respect to the arm portion 21, and a syringe ascending and descending portion 23 for transferring the syringe portion 22 in the Z-axis direction. And the syringe portion 22 comprises a nozzle portion 22a, to a pipette tip end portion of which the pipette tip 151 is detachably attached, a pump portion 22b for sucking and discharging through the nozzle portion 22a, a motor 22c for driving the pump portion 22b, a capacitance sensor 22d, and a pressure detection sensor 22e, as shown in FIG. 10. At the pump portion 22b, a suck function and a discharge function of the syringe portion 22 can be obtained by converting rotation of the motor 22c into a piston action. The capacitance sensor 22d is a capacitance type sensor and detects capacitance of the pipette tip 151 formed by a conductive resin and of liquid. The pressure detection sensor 22e detects pressure at a time of sucking and discharging by means of the pump portion 22b. Whether the sucking and discharging are surely performed or not is detected by means of the capacitance sensor 22d and the pressure detection sensor 22e.

And, a sample container setting stand 31 having five sample container setting holes 31a and a grasping portion 31b is detachably fitted into a concave portion (not shown) of the sample container setting portion 30, as shown in FIGS. 1 and 2. A sample container 32 in which soluble extract (sample) prepared by pretreating (homogenizing, percolating, and diluting) the resected tissue is contained, is set to five sample container setting holes 31a of the sample container setting stand 31, as shown in FIGS. 1 and 2.

And, a reagent container setting stand 41 having two primer reagent container setting holes 41a, an enzyme reagent container setting hole 41b, and a grasping portion 41b, is detachably fitted into a concave portion (not shown) of the reagent container setting portion 40. The primer reagent container setting holes 41a of the reagent container setting stand 41 are provided with a predetermined space therebetween along the Y-axis direction and the enzyme reagent container setting hole 41b is provided only on the left side of the front. A primer reagent container 42a in which a primer reagent of β-actin is contained and an enzyme reagent container 42b in which enzyme reagent common to cytokeratin (CK19) and β-actin is contained, are disposed on the primer reagent container setting hole 41a on the left side of the front and the enzyme reagent container setting hole 41b (see FIG. 2), respectively. And, the primer reagent container 42a in which a primer reagent of cytokeratin (CK19) is contained is disposed on the enzyme reagent container setting hole 41b on the right side of the front.

Figure 11:
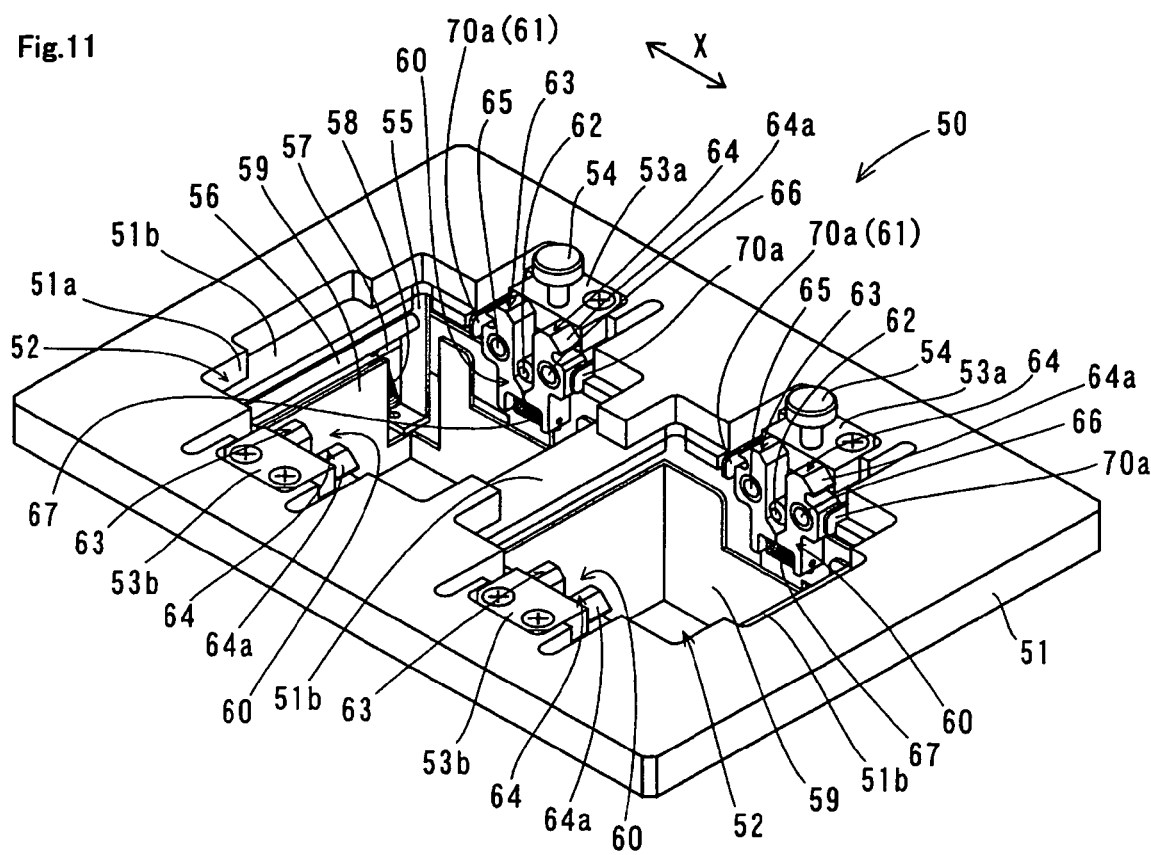
FIG. 11 is a perspective view showing a structure of a pipette tip set portion of the liquid dispensing apparatus shown in FIG. 1.
Figure 12:
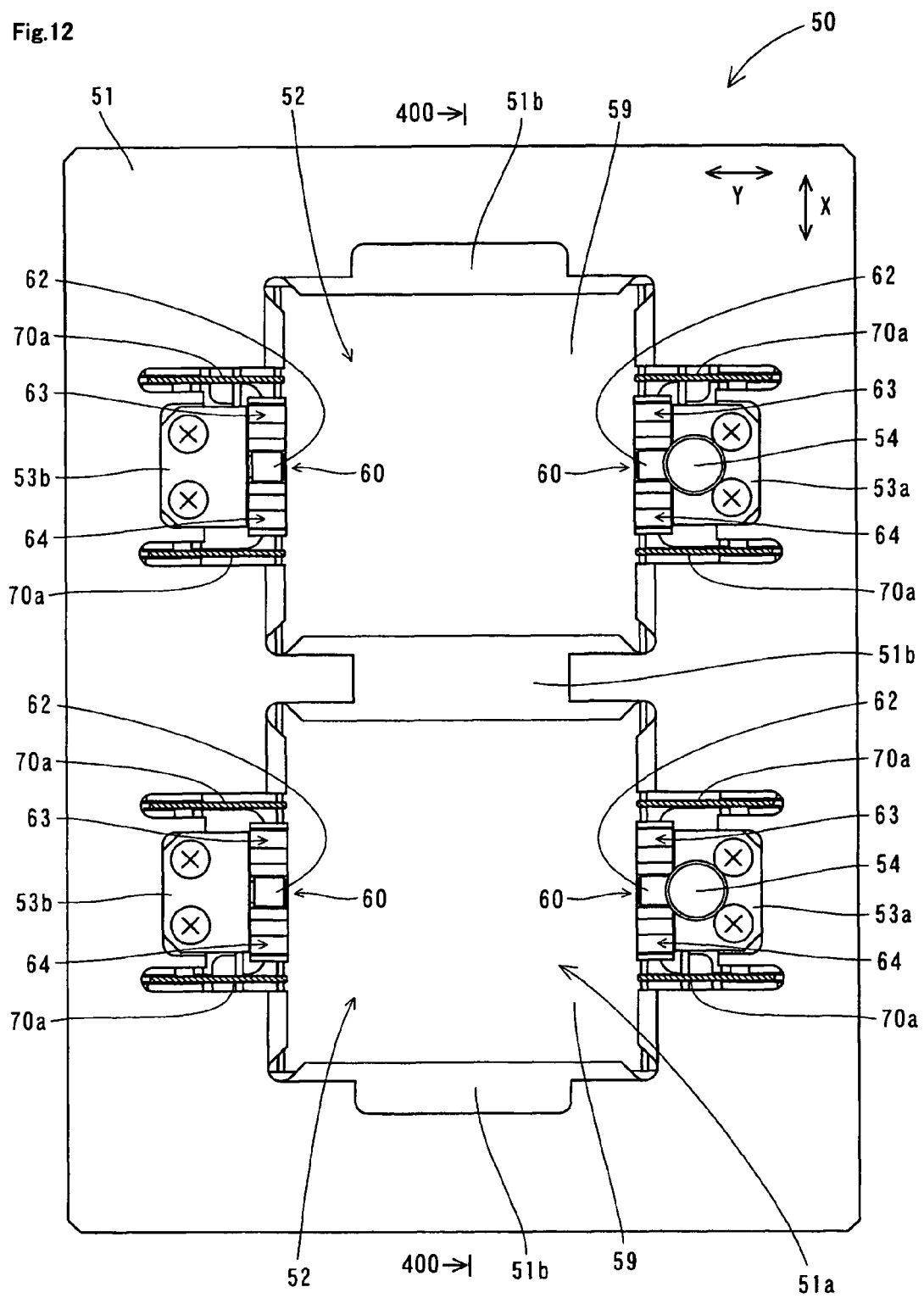
FIG. 12 is a top view showing the pipette tip set portion of the liquid dispensing apparatus shown in FIG. 11.

Next, a structure of the pipette tip set portion 50 for setting the pipette tip rack 1 will be described in reference to FIGS. 3 and 11 to 14. The pipette tip set portion 50 comprises a tabular set stand 51 having an opening 51a and two fixing mechanisms 52 attached to the opening 51a of the set stand 51, as shown in FIGS. 11 and 12. The two fixing mechanisms 52 are disposed so as to be adjacent with each other in the X-axis direction. The opening 51a is provided with three step portions 51b for supporting the engaging portion 8 of the pipette tip supporting member 4 (see FIG. 3) from below. A center step portion 51b out of the three step portions 51b is used by the engaging portions 8 of the two pipette tip supporting members 4.

Figure 13:
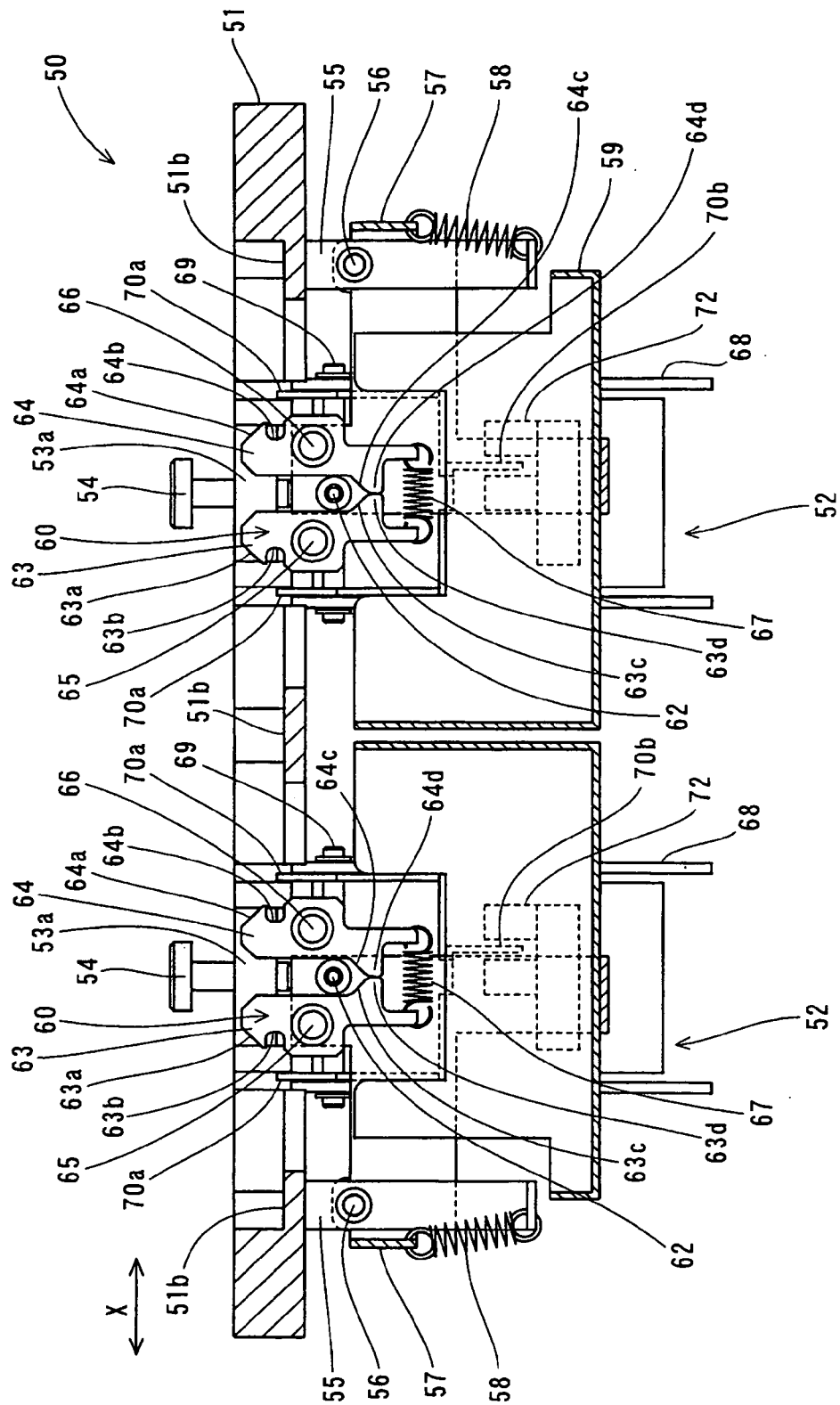
FIG. 13 is a cross-sectional view taken along a line 400-400 in FIG. 12.

And, the two fixing mechanisms 52 have a same structure, as shown in FIGS. 11 to 13. That is to say, the fixing mechanism 52 comprises a pair of brackets 53a and 53b, a detachment button 54, a supporting member 55 (see FIG. 13), a shaft 56, a rotating member 57, a tension coil spring 58, a fall preventing member 59, a pair of rack engaging portions 60, a pair of rack lifting portions 61 (see FIG. 14), as shown in FIGS. 11 to 14. The two brackets 53a and 53b are disposed on positions opposing to each other with the opening 51a of the set stand 51 interposed therebetween. The detachment button 54 is attached to the set stand 51 through the bracket 53a. The detachment button 54 is provided for making the rack body 2 of the pipette tip rack 1 which is set to the pipette tip set portion 50 detachable from the pipette tip set portion 50. The rotating member 57 is pivotably attached to the supporting member 55 by means of the shaft 56, as shown in FIG. 13. A cylindrical abutting pin 62 is attached to the rotating member 57. The rotating member 57 is energized by the tension coil spring 58 in a direction in which the abutting pin 62 lifts.

The fall preventing portion 59 is located below the opening 51a of the set stand 51, and supported by the rotating member 57 at a bottom surface thereof. The fall preventing portion 59 is provided for preventing the pipette tip 151 held within the rack body 2 of the pipette tip rack 1 from accidentally fall into an inside of the apparatus. And, the pair of rack engaging portions 60 has a same structure as shown in FIG. 12. The rack engaging portion 60 includes a pair of engaging members 63 and 64, shafts 65 and 66 for pivotably supporting the engaging members 63 and 64, and a tension coil spring 67, as shown in FIGS. 11 and 13. The pair of engaging members 63 and 64 is disposed on positions opposing to each other so as to interpose the above-described abutting pin 62 therebetween, as shown in FIG. 13. The engaging members 63 and 64 comprise slant portions 63a and 64a formed on upper end positions thereof, engaging concave portions 63b and 64b formed below the slant portions 63a and 64a for engaging with the engaging portions 8 of the pipette tip supporting member 4, and convex portions 63d and 64d having slant surfaces 63c and 64c on upper portions thereof. And, the concave portions 63d and 64d of the pair of engaging members 63 and 64 are disposed so as to face to each other such that protruding portions thereof abut against each other. The pair of engaging members 63 and 64 is energized by the tension coil spring 67 in a direction in which the convex portions 63d and 64d approach to each other around the shafts 65 and 66, which are rotation centers thereof.

Figure 14:
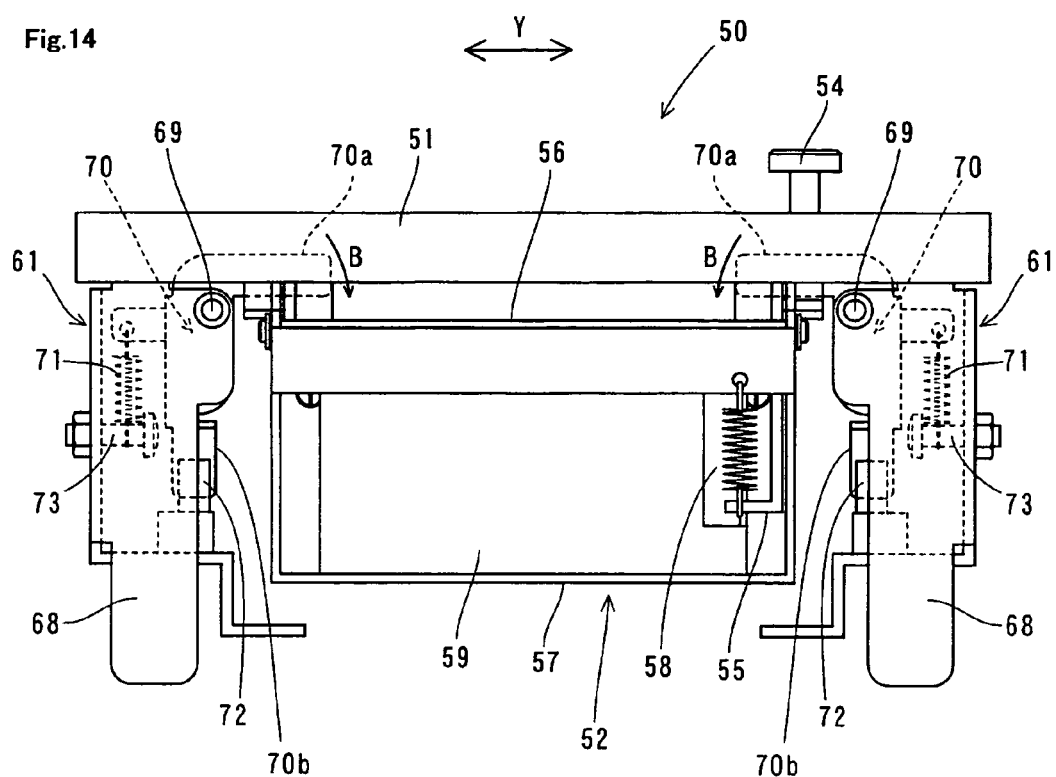
FIG. 14 is a front view showing the pipette tip set portion of the liquid dispensing apparatus shown in FIG. 11.
Figure 15:
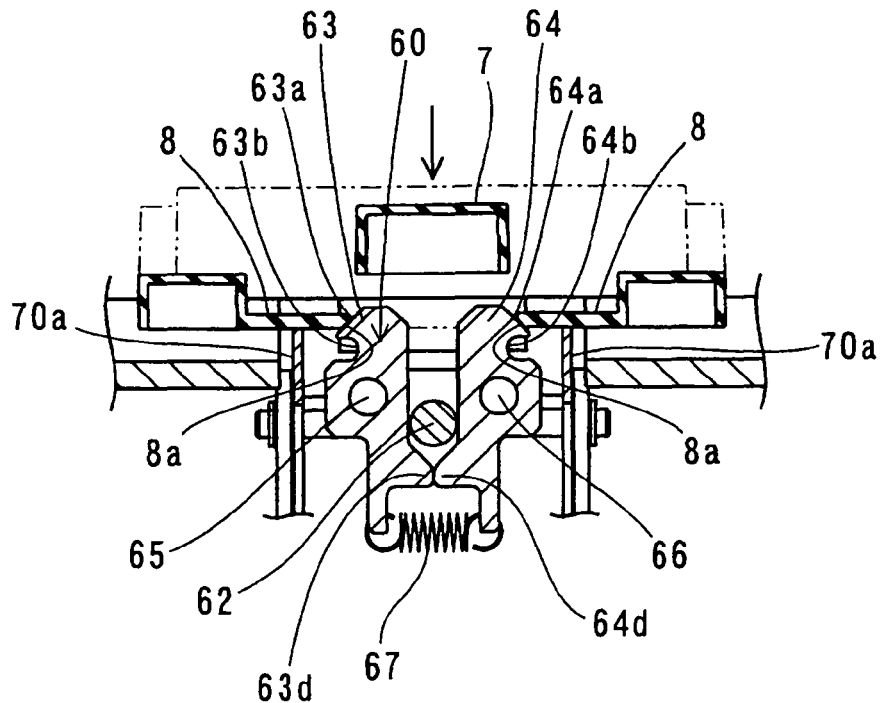
FIG. 15 is a view for describing a set action when setting the pipette tip rack according to an embodiment shown in FIG. 3 to a pipette tip set portion of a liquid dispensing apparatus.
Figure 16:
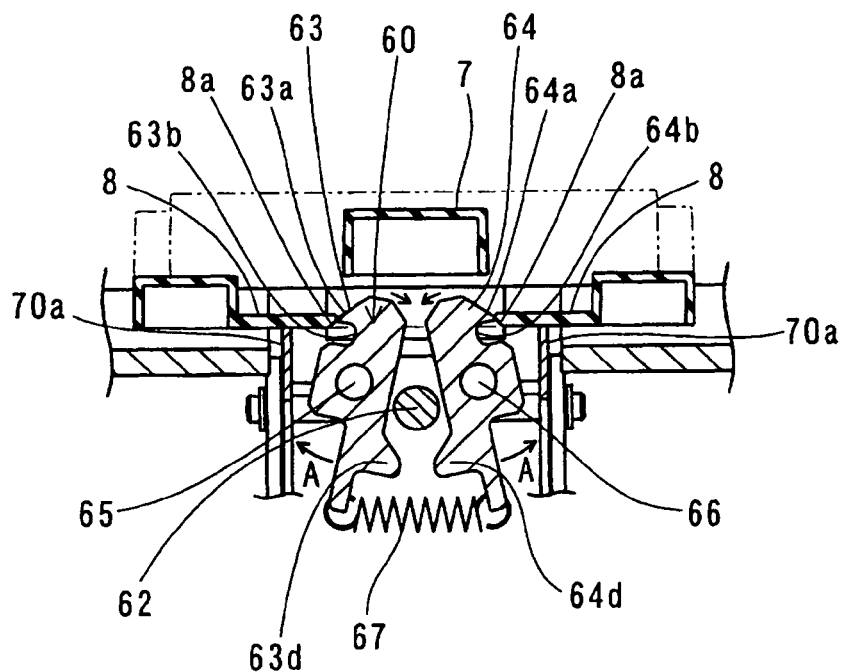
FIG. 16 is a view for describing a set action when setting the pipette tip rack according to an embodiment shown in FIG. 3 to a pipette tip set portion of a liquid dispensing apparatus.

And, a pair of rack lifting portions 61 has a same structure, as shown in FIG. 14. The rack lifting portion 61 includes a bracket 68, a shaft 69, a lifting member 70, and a tension coil spring 71. The lifting member 70 is pivotably attached to the bracket 68 around the shaft 69. The lifting member 70 serves to lift the rack body 2 upward when the rack body 2 of the pipette tip rack 1 is detached from the pipette tip set portion 50. The lifting member 70 includes a pair of lifting pieces 70a formed on an upper portion thereof and a detection piece 70b formed on a lower portion thereof. The pair of lifting pieces 70a is formed so as to extend toward the opening 51a of the set stand 51 so as to abut against the engaging portions 8 (see FIG. 3) of the rack body 2 from below, as shown in FIG. 12. The detection piece 70b is provided for detecting whether or not the pipette tip rack 1 is set to the pipette tip set portion 50.

And an optical transparent sensor 72 for detecting the detection piece 70b of the lifting member 70 is attached to the bracket 68. And the lifting member 70 is energized in a direction in which the lifting piece 70a of the lifting member 70 moves upward by the tension coil spring 71 attached to a spring attaching pin 73. And the spring attaching pin 73 is attached to the bracket 68.

And, each of the reaction detection blocks 80a of the reaction detection apparatus 80 comprises a reaction portion 81, two turbidity detection portions 82, and a lid closing mechanism portion 83, as shown in FIG. 1. Each of the reaction portions 81 is provided with two detection cell set holes 81a for setting a detection cell 85, as shown in FIG. 2.

And, the turbidity detection portion 82 comprises an LED light source portions 82a formed by a blue LED having a wavelength of 465 nm, which is attached to a substrate 84a disposed on one side surface side of the reaction portion 81, and a photodiode light receiving portion 82b attached to the substrate 84b disposed on the other side surface side of the reaction portion 81 as shown in FIG. 2. Two turbidity detection portions 82 comprising one LED light source portion 82a and one photodiode light receiving portion 82b, are provided on each of the reaction detection blocks 80a. Therefore, ten turbidity detection portions 82 comprising the LED light source portions 82a and the photodiode light receiving portions 82b are provided on five reaction detection blocks 80a. The LED light source portion 82a and the corresponding photodiode light receiving portion 82b are disposed such that the LED light source portion 82a can illuminate a lower portion of the detection cell 85 with light of a diameter of approximately 1 mm, and the photodiode light receiving portion 82b can receive the light. The LED light source portion 82a and the photodiode light receiving portion 82b serve to detect whether the detection cell 85 exists or not by intensity of the light to be received by the photodiode light receiving portion 82b, and to detect (monitor) the turbidity of the liquid contained in the detection cell 85.

And, the transfer portion 90 includes a linear motion guide 91 and a ball screw 92 for transferring the dispensing mechanism portion 20 in the Y-axis direction, a stepping motor 93 for driving the ball screw 92, a linear guide 94 and a ball screw 95 for transferring the dispensing mechanism portion 20 in the X-axis direction, and a stepping motor 96 for driving the ball screw 95, as shown in FIGS. 1 and 2. And a rail portion 91a of the linear guide 91 in the Y-axis direction and one supporting portion 92a of the ball screw 92 are attached to a frame 97, as shown in FIG. 2. And the other supporting portion 92b of the ball screw 92 is attached to the frame 97 through the stepping motor 93. And a slide portion 91b of the linear guide 91 in the Y-axis direction and a linear transfer portion (not shown) of the ball screw 92 are attached to the arm portion 21 of the dispensing mechanism portion 20. And a rail portion 94a of a linear guide 94 in the X-axis direction and one supporting portion 95a of the ball screw 95 are attached to a supporting stand 98. And a slide portion (not shown) of the linear guide 94 in the X-axis direction and the other supporting portion 95b of the ball screw 95 are attached to the frame 97. And the stepping motor 96 is attached to the other supporting portion 95b of the ball screw 95. And a transfer of the dispensing mechanism portion 20 in the X-axis and Y-axis directions is performed by rotating the ball screws 92 and 95 by means of the stepping motors 93 and 96, respectively.

And the pipette tip rejecting portion 100 is provided with two pipette tip rejecting holes 100a through which a used pipette tip 151 is rejected, as shown in FIG. 2. And a groove portion 100b having a width narrower than that of the pipette tip rejecting hole 100a is provided so as to connect to the pipette tip rejecting portion 100a.

FIGS. 15 to 19 are views for describing a set action when the pipette tip rack according to an embodiment of the present invention is set to the pipette tip set portion of the liquid dispensing apparatus. And FIG. 20 is a view for describing a detaching action when the rack body of the pipette tip rack according to an embodiment shown in FIG. 3 is detached from the pipette tip set portion of the liquid dispensing apparatus. Next, an action of the liquid dispensing apparatus (gene amplification detection apparatus) 200 according to this embodiment is described in reference to FIGS. 1 to 3, 10, and 15 to 20. The gene amplification detection apparatus according to this embodiment detects tumor-derived nucleic acid (mRNA) existing in tissue resected in a cancer operation, by amplifying the same by using a LAMP method and measuring a turbidity of a solution generated in amplification.

First, a sample container 32 in which soluble extract (sample) prepared by pretreating (homogenizing, percolating, and diluting) the resected tissue is contained, is set to the sample container setting hole 31a of the sample container setting stand 31, as shown in FIGS. 1 and 2. And the primer reagent container 42a in which the primer reagent of β-actin is contained and the enzyme reagent container 42b in which the enzyme reagent common to cytokeratin (CK19) and β-actin is contained, are set to the primer reagent container setting holes 41a on the left side of the front and the enzyme reagent container setting hole 41b, respectively. And, the primer reagent container 42a in which the primer reagent of cytokeratin (CK19) is contained is set to the primer reagent container setting hole 41b on the right side of the front.

In this embodiment, two pipette tip racks 1, each of which contains thirty-six disposal pipette tips, are fitted into the opening Sa of the pipette tip set portion 50. When the pipette tip rack 1 is set to the pipette tip set portion 50, the pipette tip rack 1 in which the lid member 3 is attached to the rack body 2 as shown in FIG. 3, is first moved to above the pipette tip set portion 50. At this time, a user grasps two opposing grasping portions 7 formed on the pipette tip supporting member 4 of the rack body 2 by two fingers or the like. And the user makes the slant portions 8a of two pairs of engaging portions 8 formed on two opposing side surfaces of the pipette tip supporting member 4 of the rack body 2 abut against the slant portions 63a and 64a of the engaging members 63 and 64 of two opposing rack engaging portions 60 of the pipette tip set portion 50. At this time, the engaging portions 8 of the rack body 2 also abut against the lifting piece 70a of each of the lifting members 70 of the rack lifting portion 61. From this state, the upper surface portion 16 of the lid member 3 of the pipette tip rack 1 is pressed downward by means of the finger or the like. Thereby, the slant portions 63a and 64a of the engaging members 63 and 64 of the rack engaging portion 60 are pressed by the slant portions 8a of the engaging portions 8 of the rack body 2, and the engaging members 63 and 64 rotate around the shafts 65 and 66, respectively in a direction indicated by arrow A, while resisting energization power of the tension coil spring 67. And, since the lifting pieces 70a of the lifting member 70 also are pressed downward by the engaging portions 8 of the rack body 2, the lifting member 70 of the rack lifting portion 61 also rotates around the shaft 69 in a direction indicated by arrow B (see FIG. 14), while resisting energization power of the tension coil spring 71.

Figure 17:
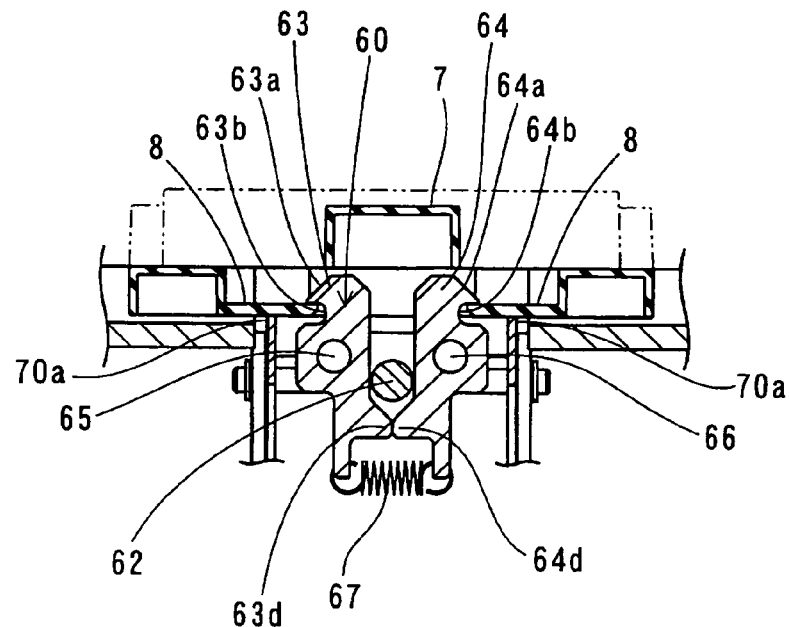
FIG. 17 is a view for describing a set action when setting the pipette tip rack according to an embodiment shown in FIG. 3 to a pipette tip set portion of a liquid dispensing apparatus.

And, four engaging portions 8 of the rack body 2 engage with the engaging concave portions 63b and 64b formed on the engaging members 63 and 64 of each of the pair of rack engaging portions 60, respectively, thereby setting the pipette tip rack 1 to the pipette tip set portion 50, as shown in FIG. 17.

Figure 18:
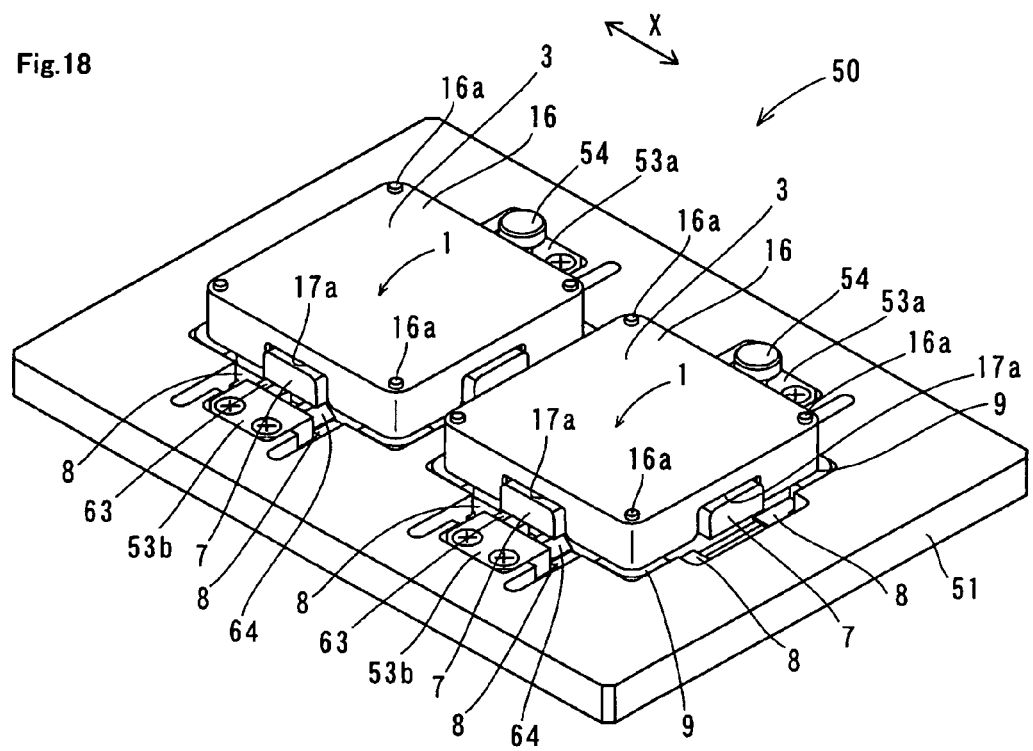
FIG. 18 is a view for describing a set action when setting the pipette tip rack according to an embodiment shown in FIG. 3 to a pipette tip set portion of a liquid dispensing apparatus.
Figure 19:
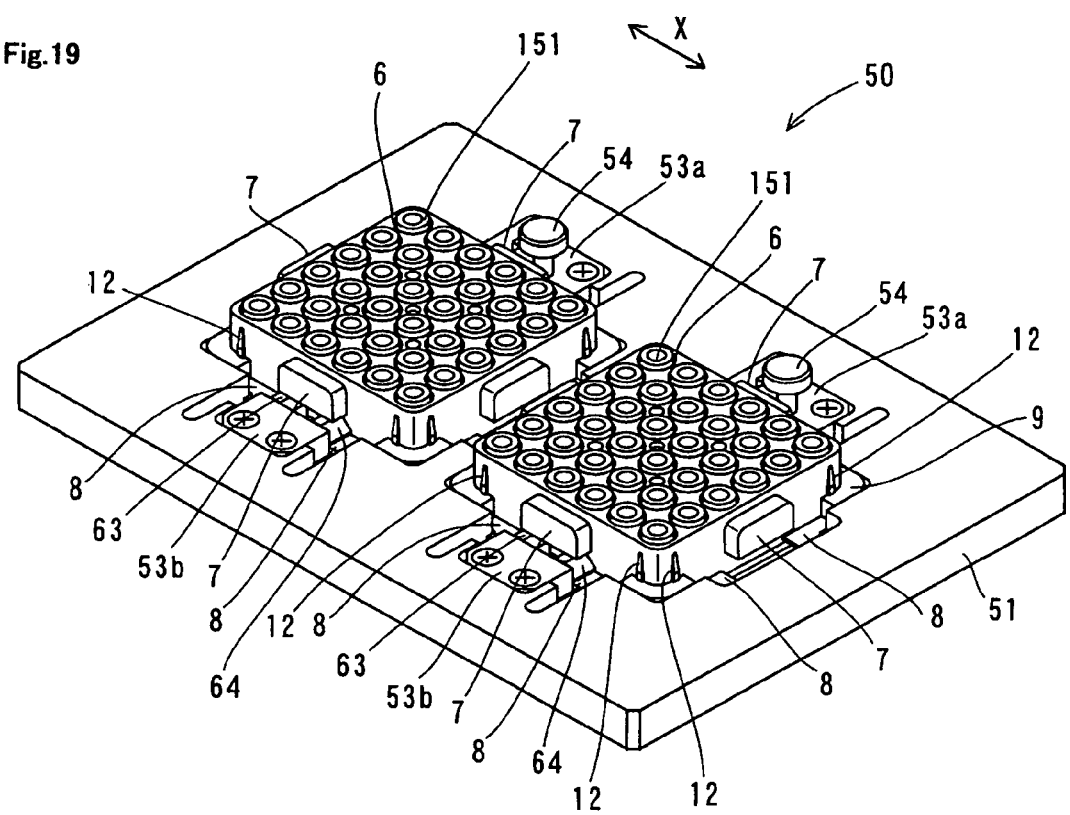
FIG. 19 is a view for describing a set action when setting the pipette tip rack according to an embodiment shown in FIG. 3 to a pipette tip set portion of a liquid dispensing apparatus.
Figure 20:
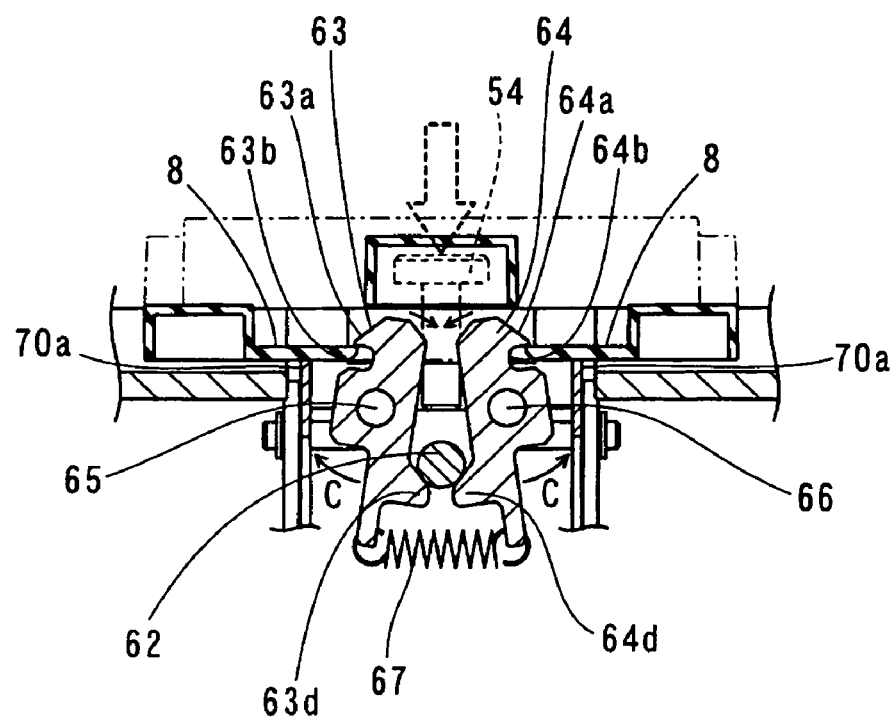
FIG. 20 is a view for describing a detaching action when detaching a rack body of the pipette tip rack according to an embodiment shown in FIG. 3 from a pipette tip set portion of a liquid dispensing apparatus.

And, the lid member 3 of the pipette tip rack 1 shown in FIG. 18 is detached from the rack body 2, thereby exploding the pipette tip 151 contained in the rack body 2 as shown in FIG. 19. In this case, since a primary position (original position) of the arm portion 21 of the dispensing mechanism portion 20 deviates from above the pipette tip set portion 50, two pipette tip racks 1 are easily fitted into the pipette tip set portion 50.

Furthermore, two cell portion 86a of the detection cell 85 are set to two detection cell set holes 81a of the reaction portion 81 of each of the reaction detection blocks 80a.

Then an action of the liquid dispensing apparatus (gene amplification detection apparatus) 200 shown in FIG. 1 is started. First, the arm portion 21 of the dispensing mechanism portion 20 is moved from the primary position to the pipette tip set portion 50 by means of the transfer portion 90. Then, the syringe ascending and descending portion 23 is driven to move downward, so that two syringe portions 22 of the dispensing mechanism portion 20 are moved downward at the pipette tip set portion 50 (see FIG. 2).

A pipette tip end of the nozzle portion 22a of the syringe portion 22 is pressed into an upper opening of the pipette tip 151, thereby attaching the pipette tip 151 to the pipette tip end of the nozzle portion 22a of each of two syringe portions 22 as shown in FIG. 10. And, after the two syringe portions 22 are moved upward, the arm portion 21 of the dispensing mechanism portion 20 is moved in the X-axis direction toward above the two primer reagent containers 42a into which the primer reagent of CK19 and that of β-action is contained, which are set to the reagent container set stand 41 by means of the transfer portion 90. And, the two syringe portions 22 are moved downward, thereby inserting the pipette tip ends of the two pipette tip 151 attached to the nozzle portions 22a of two syringe portions 22 into surfaces of the primer reagent of CK19 and that of β-action in the two primer reagent containers 42a. And, the primer reagent of CK19 and that of β-action in the two primer reagent container 42a are sucked by the pump portions 22b of the syringe portions 22.

When sucking the primer reagent, it is detected whether the pipette tip end of the pipette tip 151 formed by a conductive resin contacts the liquid surface or not by the capacitance sensor 22d (see FIG. 10), and, a sucking pressure by the pump portion 22b is detected by the pressure detection sensor 22e (see FIG. 10). By the capacitance sensor 22d and the pressure detection sensor 22e, it is detected whether or not suction is surely performed.

After the primer reagent is sucked, the two syringe portions 22 are moved upward, and then the arm portion 21 of the dispensing mechanism portion 20 is moved above the reaction detection block 80a located on an innermost side (back side of the apparatus as seen from a front surface thereof) by the transfer portion 90. And at an innermost reaction detection block 80a, the two syringe portions 22 are moved downward, thereby inserting the two pipette tip 151 attached to the nozzle portions 22a of the two syringe portions 22 into the two cell portions 86a of the detection cell 85, respectively. And, the two primer reagents of CK19 and of β-action are discharged to the two cell portions 86a, respectively, by using the pump portions 22b of the syringe portions 22. When discharging (exhausting), as well as when sucking as described above, it is detected whether the pipette tip end of the pipette tip 151 formed by the conductive resin contacts the liquid surface or not (liquid level detection) by the capacitance sensor 22d (see FIG. 10), and discharging pressure by the pump portion 22b is detected by the pressure detection sensor 22e. By the capacitance sensor 22d and the pressure detection sensor 22e, it is detected whether or not a discharge is surely performed.

In addition, when sucking and discharging an enzyme reagent and the sample to be described later, the liquid level detection by the capacitance sensor 22d and the detection by the pressure detection sensor 22e are performed as described above.

After the primer reagent is discharged, the two syringe portions 22 are moved upward, and then the arm portion 21 of the dispensing mechanism portion 20 is moved in the X-direction toward above the pipette tip rejecting portion 100 by the transfer portion 90. And the pipette tip 151 is rejected at the pipette tip rejecting portion 100. Specifically, the two syringe portions 22 are moved downward, thereby inserting the pipette tip 151 into the two pipette tip rejecting holes 100a (see FIG. 2) of the pipette tip rejecting portion 100. In this state, the arm portion 21 of the dispensing mechanism portion 20 is transferred in the Y-axis direction by the transfer portion 90, thereby moving the pipette tip 151 under the groove portion 100b. And, since the flange portion 151b on an upper surface of the pipette tip 151 abuts against lower surfaces of both sides of the groove portion 100b and receives downward force from the lower surface by moving upward and downward the two syringe portions 22, the pipette tip 151 automatically get out of the nozzle portions 22a of the two syringe portions 22. Thereby, the pipette tip 151 is rejected to the pipette tip rejecting portion 100. While the pipette tip 151 rejected to the pipette tip rejecting portion 100 is directly rejected in this embodiment, the pipette tip may be washed and reused.

Next, the arm portion 21 of the dispensing mechanism portion 20 is moved again to the pipette tip set portion 50 by the transfer portion 90. After the syringe portion 22 is moved to the pipette tip set portion 50, two new pipette tip 151 are automatically attached to the pipette tip end of the nozzle portions 22a of the two syringe portions 22 by the same action as described above. And, the arm portion 21 of the dispensing mechanism portion 20 is moved in the X-axis direction toward above the enzyme reagent container 42b in which the enzyme reagent common to CK19 and β-action is contained, which is set to the reagent container set stand 41, by the transfer portion 90, then the enzyme reagent in the enzyme reagent container 42b is sucked. Specifically, one of the syringe portions 22 located above the enzyme reagent container 42b is first moved downward to suck the enzyme reagent, and the syringe portion 22 is moved upward. Then the arm portion 21 of the dispensing mechanism portion 20 is moved in the Y-axis direction by the transfer portion 90 such that the other syringe portion 22 locates above the same enzyme reagent container 42b. And, after the other syringe portion 22 is moved downward to suck the enzyme reagent from the same enzyme reagent container 42b, the other syringe portion 22 is moved upward. And after the arm portion 21 of the dispensing mechanism portion 20 is moved above the innermost reaction detection block 80a by the transfer portion 90, the enzyme reagent common to CK19 and β-actin is discharged to the two cell portions 86a of the detection cell 85. And, after the enzyme reagent is discharged, the arm portion 21 of the dispensing mechanism portion 20 is moved above the pipette tip rejecting portion 100 by the transfer portion 90, then the pipette tip 151 is rejected.

Next, after the arm portion 21 of the dispensing mechanism portion 20 is moved again to the pipette tip set portion 50 by the transfer portion 90, new two pipette tip 151 are automatically attached to the pipette tip end of the nozzle portions 22a of the two syringe portions 22. And after the arm portion 21 of the dispensing mechanism portion 20 is moved in the X-direction toward above the sample container 32 in which the sample is contained, which is set to the sample container set stand 31 by the transfer portion 90, the sample in the sample container 32 is sucked by the same action as a suck action of the above described enzyme reagent. Then, after the arm portion 21 of the dispensing mechanism portion 20 is moved above the innermost reaction detection block 80a by the transfer portion 90, the two syringe portions 22 are moved downward to discharge the same sample to the two cell portions 86a of the detection cell 85.

By repeating the suck action and the discharge action plural times by using the pump portions 22b of the two syringe portions 22 when the sample is discharged to the two cell portions 86a of the detection cell 85, the primer reagents and the enzyme reagents of CK19 and of β-actin contained within the two cell portions 86a and the sample are stirred. A liquid temperature in the detection cell 85 is held approximately 20° C., when the primer reagents, enzyme reagents, and samples are dispensed. Then, after the arm portion 21 of the dispensing mechanism portion 20 is moved above the pipette tip rejecting portion 100 by the transfer portion 90, the pipette tip 151 is rejected.

After the primer reagent, the enzyme reagent, and the sample are discharged to the above-described cell portions 86a, a lid closing action of the lid portion 87a of the detection cell 85 is performed. After having performed the lid closing action, target nucleic acid (mRNA) is amplified by the LAMP reaction by raising the liquid temperature in the detection cell 85 from approximately 20° C. to approximately 65° C. And white turbidity by magnesium pyrophosphate generated by the amplification is detected. Specifically, detection of liquid turbidity is performed by real-time monitoring of the liquid turbidity in the detection cell 85 at the time of amplification reaction by using the LED light source portion 82a and the photodiode light receiving portion 82b shown in FIG. 3.

It is required to detach the rack body from the pipette tip set portion 50 in a case in which all the thirty-six pipette tip 151 of the rack body 2 set to the pipette tip set portion 50 are used. The detachment button 54 provided on the pipette tip set portion 50 is pressed downward by means of fingers or the like, as shown in FIG. 20 to detach the rack body 2 from the pipette tip set portion 50. Thereby, the abutting pin 62 attached to the rotating member 57 of the pipette tip set portion 50 abuts the slant surfaces 63c and 64c of the convex portions 63d and 64d of a pair of engaging members 63 and 64 of the rack engaging portion 60 at a same time. And the pair of engaging members 63 and 64 of the rack engaging portion 60 rotates around the shafts 54 and 66, respectively, in a direction indicated by arrow C in FIG. 20 while resisting energization power of the tension coil spring 67. Thereby, engaging state of two pairs of engaging portions 8 of the rack body 2 with the engaging concave portions 63b and 64b each of the engaging members 63 and 64 of the two rack engaging portions 60. At this time, since the rack body 2 receives upward energization power by each of the lifting members 70 of a pair of rack lifting portions 61, the body is moved upward at the same time as the engaging state is released. Then, the user detaches the rack body 2 from the pipette tip set portion 50 by grasping two opposing grasping portions 7 formed on the pipette tip supporting member 4 of the rack body 2 by means of two fingers or the like. The above-described detaching action of the rack body 2 from the pipette tip set portion 50 can be performed during operation of the liquid dispensing apparatus 200.

In this embodiment, as described above, the rack body 2 is provided with the pipette tip housing member 5 for housing the pipette tip end of the pipette tip 151 supported by the pipette tip supporting member 4 of the rack body 2, thereby closing the pipette tip end of the pipette tip 151 supported by the pipette tip supporting member 4 from outside with the pipette tip housing member 5 interposed therebetween, so that attachment of contaminant including a degrading enzyme such as saliva of human beings is inhibited. Therefore, the pipette tip end of the pipette tip 151 is prevented from contaminating.

And in this embodiment, as described above, the lid member 3 attached to the rack body 2 for covering the flange portion 151b of the pipette tip 151 supported by the supporting member 4 of the rack body 2, thereby closing the flange portion 151b of the pipette tip 151 supported by the pipette tip supporting member 4 of the rack body 2 from outside with the lid member 3 interposed therebetween, so that attachment of contaminant including a degrading enzyme such as saliva of human beings, is inhibited. Therefore, the flange portion 151b of the pipette tip 151 is prevented from contaminating.

In addition, in this embodiment, since the user can grasp the grasping portion 7 of the rack body 2 when the pipette tip rack 1 is set to the liquid dispensing apparatus 200, by providing grasping portions 7 on a pair of opposing side surfaces of the rack body 2, the pipette tip rack 1 in which the lid member 3 is attached to the rack body 2 is easily grasped to be set to the liquid dispensing apparatus 200.

And in this embodiment, as described above, since the grasping portion 7 of the rack body 2 and the notch 17a of the lid member 3 can engage with each other with a predetermined allowance (space S) therebetween, by forming the notch 17a so as to have a predetermined allowance (space S) between the same and the grasping portion 7 of the rack body 2 when the notch 17a formed on the side surface portion 17 of the lid member 3 and the grasping portion 7 of the rack body 2 engage with each other, the rack body 2 is prevented from moving according to a move of the lid member 3 when the lid member 3 is detached from the rack body 2 after the pipette tip rack 1 is set to the liquid dispensing apparatus 200. Thereby, the lid member 3 is easily detached from the rack body 2 after the pipette tip rack 1 is set to the liquid dispensing apparatus 200.

The embodiment disclosed above has been described by way of examples in all aspects and is not to be considered as restrictive in any sense. The scope of the present invention is expressed by the scope of the claims and not by the description of the embodiment. The present invention may be variously modified insofar as such modification is within the scope and equivalences of the claim.

For example, while the present invention is applied to the pipette tip rack used in the gene amplification detection apparatus (liquid dispensing apparatus) in which the target nucleic acid is amplified by the LAMP method in the above-described embodiment, the present invention is also applicable to a pipette tip rack used in a gene amplification detection apparatus (liquid dispensing apparatus) in which the target nucleic acid is amplified by polymerase chain reaction method (PCR method) or ligase chain reaction method (LCR method), and to a pipette tip rack used for liquid dispensing apparatus other than the gene amplification detection apparatus.

And, while an example in which the lid member has a side surface portion is shown in the above-described embodiment, the lid member may comprised of only an upper surface portion in the present invention. In this case, a wall portion to enclose a plurality of pipette tip inserting portion formed on the pipette tip supporting member of the rack body is preferably formed on the pipette tip supporting member.

In addition, while the rack body and the lid member are formed in square as seen from above, the body can be formed in rectangular or oval other than square, in the present invention.

And, while an example in which the lid member and the pipette tip housing member are formed by a semitransparent material is shown in the above-described embodiment, the lid member and the pipette tip housing member can be formed by a transparent material or by a material in which the inside of the members are invisible from the outside.

What is claimed is:

1. A pipette tip rack for detachably housing a plurality of pipette tips used in an automatic liquid dispensing apparatus for dispensing liquid comprising:
   a rack body comprising a pipette tip supporting portion for detachably supporting the pipette tips, and a pipette tip housing portion disposed below the pipette tip supporting portion, the pipette tip supporting portion being substantially square and having a plurality of pipette tip inserting holes disposed in a matrix arrangement such that longitudinal disposition and lateral disposition thereof are substantially equivalent; and
   a lid member that is placed onto the pipette tip supporting portion for covering root portions of the pipette tips inserted into the holes, and being substantially square,
   wherein the pipette tip supporting portion includes four side walls, each of which includes a pair of lower protruding portions for fixing the pipette tip supporting portion to the automatic liquid dispensing apparatus and an upper protruding portion to be grasped by a user;
   the pair of lower protruding portions are arranged on a lower end position of the side wall so as to protrude outwardly from the side wall;
   the upper protruding portion is arranged on the side wall so as to protrude outwardly from the side wall, a position of the upper protruding portion being upper than the pair of lower protruding portions and center of the side wall in a transverse direction;
   the lid member has four notches configured such that the four upper protruding portions are inserted into the four notches when the lid member is placed onto the pipette tip supporting portion; and
   the four upper protruding portions protrude outwardly from the lid member through the four notches in a state in which the lid member is placed onto the pipette tip supporting portion.

2. The pipette tip rack according to claim 1, wherein the lid member includes four side walls, each of which includes one of said four notches.

3. The pipette tip rack according to claim 1, wherein the four notches engage with the four upper protruding portions in the state in which the lid member is placed onto the pipette tip supporting portion.

4. The pipette tip rack according to claim 3, wherein a predetermined space exists between each of said four notches and each of said four upper protruding portions when each of said four notches engage with each of said four upper protruding portions.

5. The pipette tip rack according to claim 1, further comprising a plurality of pipette tips inserted into the plurality of pipette tip inserting holes,
wherein the pipette tip housing portion of the rack body is disposed below the pipette tip supporting portion housing when the plurality of pipette tips are in a state in which a pipette tip end
portion of each of the plurality of pipette tips are inserted into the plurality of pipette tip inserting holes and do not contact an inner side of the pipette tip housing portion.

6. The pipette tip rack according to claim 1,
wherein the pipette tip supporting portion has a first engaging portion that engages with the pipette tip housing portion,
the pipette tip housing portion has a second engaging portion that engages with the first engaging portion of the pipette tip supporting portion, and
the pipette tip housing portion is attached below the pipette tip supporting portion by engaging the second engaging portion with the first engaging portion.

7. The pipette tip rack according to claim 6,
wherein the pipette tip supporting portion is integrally provided with a deflection preventing portion for preventing a side surface of the pipette tip housing portion from inwardly deflecting.

8. The pipette tip rack according to claim 1,
wherein at least one of the pipette tip housing portion and the lid member is formed from a material in which an inside thereof is visible from an outside.

9. A pipette tip assembly used in an automatic liquid dispensing apparatus for dispensing liquid comprising:
a rack body comprising a pipette tip supporting portion for detachably supporting the pipette tips, and a pipette tip housing portion disposed below the pipette tip supporting portion, the pipette tip supporting portion being substantially square and having a plurality of pipette tip inserting holes disposed in a matrix arrangement such that longitudinal disposition and lateral disposition thereof are substantially equivalent;
a lid member that is placed onto the pipette tip supporting portion for covering root portions of the pipette tips inserted into the holes, and being substantially square; and
a pipette tip to be inserted into the pipette tip inserting hole of the pipette tip supporting portion held by the pipette tip housing portion,
wherein the pipette tip supporting portion includes four side walls, each of which includes a pair of lower protruding portions for fixing the pipette tip supporting portion to the automatic liquid dispensing apparatus and an upper protruding portion to be grasped by a user;
the pair of lower protruding portions are arranged on a lower end position of the side wall so as to protrude outwardly from the side wall;
the upper protruding portion is arranged on the side wall so as to protrude outwardly from the side wall, a position of the upper protruding portion being upper than the pair of lower protruding portions and center of the side wall in a transverse direction;
the lid member has four notches configured such that the four upper protruding portions are inserted into the four notches when the lid member is placed onto the pipette tip supporting portion; and
the four upper protruding portions protrude outwardly from the lid member through the four notches in a state in which the lid member is placed onto the pipette tip supporting portion.

\* \* \* \* \*